United States Patent [19]

Adachi et al.

[11] Patent Number: 4,703,051
[45] Date of Patent: Oct. 27, 1987

[54] 4,7-DIHYDROTHIENO[2,3-B]PYRIDINE DERIVATIVES USEFUL IN THE TREATMENT OF CARDIOVASCULAR DISEASES

[75] Inventors: Ikuo Adachi; Yoshiharu Hiramatsu; Motohiko Ueda, all of Osaka; Masaru Kawakami, Hyogo, all of Japan

[73] Assignee: Shionogi & Co., Ltd., Osaka, Japan

[21] Appl. No.: 876,120

[22] Filed: Jun. 2, 1986

[30] Foreign Application Priority Data

Jul. 3, 1985 [JP] Japan .................. 60-147054

[51] Int. Cl.$^4$ .................. A61K 31/44; C07D 495/04
[52] U.S. Cl. .................. 514/291; 514/301; 546/80; 546/114
[58] Field of Search ............ 546/80, 114; 514/291, 514/301

[56] References Cited

U.S. PATENT DOCUMENTS 4,532,248 7/1985 Franchowiak et al. ............ 514/302
4,562,256 12/1985 Adachi et al. .................. 546/120

*Primary Examiner*—John M. Ford
*Assistant Examiner*—Bernard I. Dentz
*Attorney, Agent, or Firm*—Wenderoth, Lind & Ponack

[57] ABSTRACT

Highly effective calcium channel blockers having potent antihypertensive and coronary vasodilating actions, i.e. 4,7-dihydrothieno[2,3-b]pyridine derivatives of the formula:

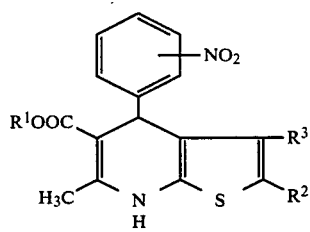

wherein $R^1$ is straight or branched chain $C_1$–$C_4$ alkyl, alkoxyalkyl, or arylalkyl; $R^2$ is hydrogen, straight or branched chain $C_1$–$C_4$ alkyl, or alkoxycarbonyl; $R^3$ is hydrogen, straight or branched chain $C_1$–$C_4$ alkyl, phenyl which may be substituted by one or more halogens or alkoxy groups, optionally substituted cycloalkyl, or optionally substituted cycloalkylalkyl; or $R_2$ and $R_3$ taken together may form an alkylene.

9 Claims, No Drawings

4,7-DIHYDROTHIENO[2,3-B]PYRIDINE DERIVATIVES USEFUL IN THE TREATMENT OF CARDIOVASCULAR DISEASES

BACKGROUND OF THE INVENTION

1. Field of the Invention

The compounds provided by the present invention are classified into a group of calcium channel blockers (hereinafter referred to as Ca-blockers), and have potent antihypertensive and coronary vasodilating actions which last for hours. These compounds are useful in the treatment of cardiovascular diseases such as angina pectoris, hypertention, cerebrovascular dysfunction, arrhythmia or the like, and have the advantage that they have no systole inhibitory action as an advese reaction usually seen in the use of the analogous known-compounds.

2. Prior Art

Compounds having Ca-blocking, effect have commonly been used in the treatment of cardiovascular diseases such as angina pectoris, hypertention, cerebrovascular dysfunction, arrhythmia or the like, and have become well-known because of their high efficacy. In particular, a series of 1,4-dihydropyridine derivatives have been extensively researched and developed as Ca-blockers. Examples of useful Ca-blockers are Nifedipine (U.S. Pat. Nos. 3,485,847 and 3,644,627), Nisoldipine (Japanese Patent Publication No. 56-47185), 2-amino-1,4-dihydropyridine derivatives (JPN Pat. Pub. No. 57-20306), Nicardipine (JPN Unexam. Pat. Pub. No. 49-109384), and the like. Some examples of pyrazolodihydropyrindine derivatives, the production thereof and their Ca-blocking action are disclosed in JPN Unexam. Pat. Pub. No. 59-118786 and in JPN Unexam. Pat. Pub. No. 59-65089 and JPN Pat. Appln. Nos. 58-166258 and 59-53118 by the present inventors.

SUMMARY

The present invention relates to 4,7-dihydrothieno-[2,3-b]pyridine derivatives, the process for production thereof, and agents for cardiovascular diseases. More particularly, it provides 4,7-dihydrothieno[2,3-b]pyridine derivatives of the formula:

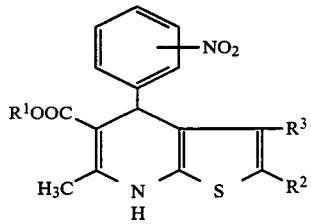

wherein $R^1$ is straight or branched chain $C_1-C_4$ alkyl, alkoxyalkyl, or arylalkyl; $R^2$ is hydrogen straight or branched chain $C_1-C_4$ alkyl, or alkoxycarbonyl; $R^3$ is hydrogen, straight or branched chain $C_1-C_4$ alkyl, phenyl which may be substituted by one or more halogens or alkoxy groups, optionally substituted cycloalkyl, or optionally substituted cycloalkylalkyl, or $R^2$ and $R^3$ taken together may form an alkylene; a process for production of 4,7-dihydrothieno[2,3-b]pyridine derivatives of the formula:

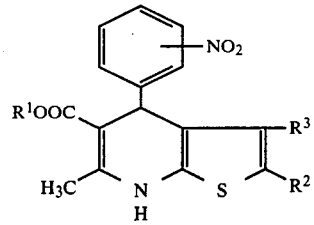

wherein $R^1$, $R^2$, $R^3$ each is the same as above, comprising reacting a compound of the formula:

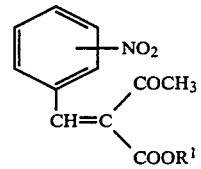

wherein $R^1$ is the same as above, with a compound of the formula:

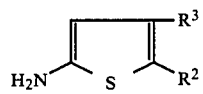

wherein $R^1$ and $R^2$ each is the same as above; and agents for cardiovascular diseases comprising containing at least one of the 4,7-dihydrothieno[2,3-b]pyridine derivatives of the formula:

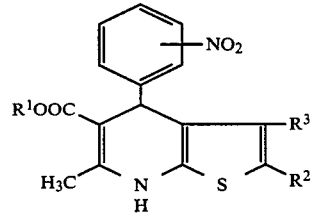

wherein $R^1$, $R^2$, and $R^3$ each is the same as above.

DESCRIPTION OF PREFERRED EMBODIMENTS

The objective compounds (I) of this invention are prepared through the Michael addition between heterocyclic amines and α,β-unsaturated ketones accompanied by cyclization reaction.

Problems to be Resolved

As mentioned above, many Ca-blocking agents are widely used in the treatment of cardiovascular diseases but highly safe and long-acting ones have not been launched in the market. Such a compound, therefore, has long been desired.

Preferred Embodiment of the Invention

Means to Resolve the Problems

In this invention, the straight or branched chain $C_1-C_4$ alkyl includes, for example, methyl, ethyl, n-propyl, i-propyl, n-butyl, i-butyl, s-butyl, and t-butyl; the alkoxyalkyl means C₁–C₄ alkyl substituted by lower alkyloxy and includes, for example, methoxymethyl, ethoxymethyl, methoxyethyl, ethoxyethyl, propoxyethyl, i-propoxyethyl, butoxyethyl, t-butoxyethyl, methoxypropyl, ethoxypropyl, propoxypropyl, t-butoxypropyl, methoxybutyl, i-butoxybutyl, and the like.

Arylalkyl means $C_1$–$C_5$ alkyl substituted by phenyl which may have one or two substituents wherein the substituent means halogen or lower alkoxy and $C_1$–$C_5$ alkyl means straight alkyl. Arylalkyl includes, for example, benzyl, phenethyl, phenylpropyl, phenylbutyl, phenylpentyl, and the like.

Alkoxycarbonyl means carbonyl substituted by a lower alkoxy and includes, for example, methoxycarbonyl, ethoxycarbonyl, propoxycarbonyl, i-propoxycarbonyl, butoxycarbonyl, t-butoxycarbonyl, and the like.

Phenyl which may be substituted by one or more halogen or alkoxy group means phenyl which may be substituted by one or two halogens or lower alkoxys wherein halogen includes fluorine, chlorine, and bromine and lower alkoxy includes methoxy, ethoxy, and the like: they may be the same or different each other.

Optionally substituted cycloalkyl means $C_3$–$C_7$ cycloalkyl substituted or unsubstituted by, for example, lower alkyl such as methyl, ethyl, propyl, butyl, and pentyl. It includes cyclobutyl, cyclopentyl, cycohexyl, 2-i-propyl-4-methylcyclohexyl, and the like.

In the word "optionally substituted cycloalkylalkyl", cycloalkylalkyl means $C_1$–$C_4$ alkyl substituted by $C_3$–$C_7$ cycloalkyl wherein $C_3$–$C_7$ cycloalkyl includes cyclopropyl, cyclobutyl, cyclopentyl, cyclohexyl, and cycloheptyl; and $C_1$–$C_4$ alkyl includes methyl, ethyl, propyl, butyl, and the like.

Alkylene means alkylene of the formula:

—(CH₂)ₙ— wherein n is an integer of 3 to 6, formed by combination of $R^2$ with $R^3$. Especially, butylene (n=4) is most preferably employed.

The compound (I) of the present invention can readily be produced by the reaction of an α,β-unsaturated ketone reagent (II) with a 5-aminothiophene (III), as shown in the following scheme:

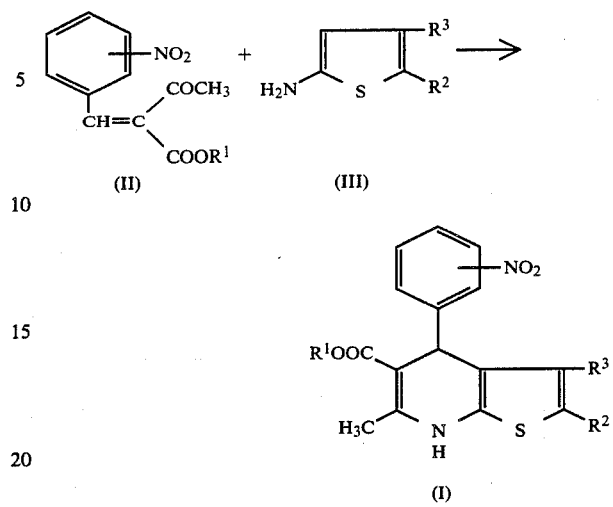

wherein $R^1$, $R^2$, and $R^3$ each is the same as defined above.

This reaction may be carried out in the presence or absence of any solvent. As a solvent used in the reaction, the following are exemplified: alcohols such as methanol, ethanol, isopropanol, tert-butanol, ethylene glycol, and the like; hydrocarbons such as benzene, toluene, xylene, and the like; ethers such as diethyl ether, tetrahydrofuran, dioxane, glyme, diglyme, and the like; halogenated hydrocarbons such as dichloromethane, chloroform, dichloroethane, carbon tetrachloride, and the like; esters such as ethyl acetate and the like; acetic acid; dimethylformamide; pyridine; and the like solvent. An acid or organic base may be employed if necessary. The acid includes, for example, inorganic acids such as sulfuric acid, hydrochloric acid, and phosphoric acid; organic acids such as paratoluenesulfonic acid, acetic acid, and formic acid; and Lewis acids such as boron trifluoride, zinc chloride, aluminium chloride, magnesium chloride, and tin chloride. The organic base includes, for example, triethylamine, pyridine, pyrrolidine, piperidine, and the like. The reaction is performed for a period of several hours to several days at around room temperature (1°–30° C.) or under heating (30°–100° C.).

One of the starting materials, an α,β-unsaturated ketone reagent (II) employed in the reaction is known and can be prepared according to the manner disclosed in the JPN Unexam. Pat. Pub. No. 59-65089. The other 5-aminothiophenes (III) can be prepared according to the reaction sequence as shown below.

Production of 5-aminothiophenes (III)

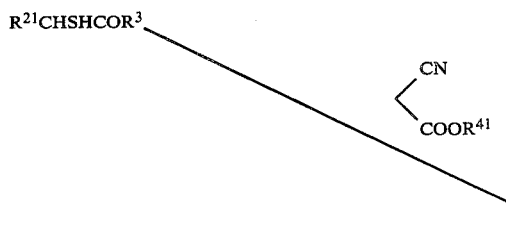

Production of 5-aminothiophenes (III)

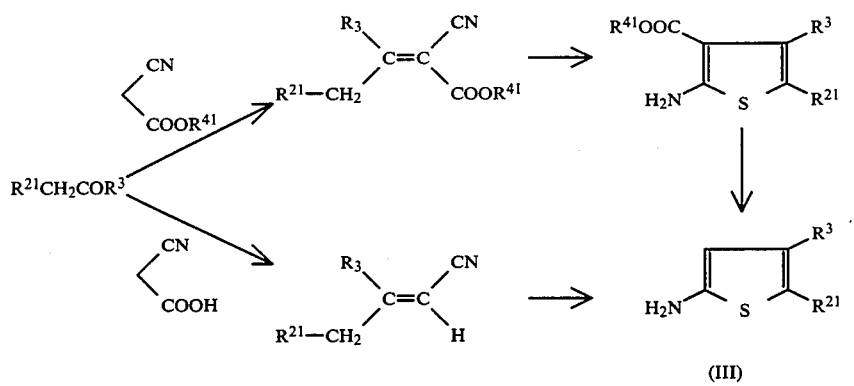

(III)

wherein $R^{21}$ is hydrogen, alkoxycarbonyl, or alkyl; $R^3$ is the same as defined above or $R^3$ and $R^{21}$ taken together may form an alkylene; and $R^{41}$ is alkyl.

Each step in the reaction sequence may be performed under the conditions of the following disclosures: K. Gewald et al., Chemishe Berichte 98, 3571 (1965); ibid, 99 94 (1966); ibid, 99 2712 (1966); K. Gewald et al., Journal für Praktishe Chemie, 315, 539 (1973); O. Yonemitsu et al., Journal of Organic Chemistry, 43, 2087 (1978); Masaki Ohta, Journal of the Pharmaceutical Society of Japan, 70, 709 (1950); and K. Kariyone et al., ibid, 79, 711 (1959).

Typical compounds of this invention which are prepared from the starting materials, α,β-unsaturated ketone reagents (II) and 5-aminothiophenes (III) in the aformentioned manner are shown below.

Methyl 4,7-dihydro-6-methyl-4-(3-nitrophenyl)-3-phenylthieno[2,3-b]pyridine-5-carboxylate,
Phenethyl 4,7-dihydro-6-methyl-4-(3-nitrophenyl)-3-phenylthieno[2,3-b]pyridine-5-carboxylate,
Methyl 4,7-dihyro-6-methyl-4-(3-nitrophenyl)-3-(4-chlorophenyl)thieno[2,3-b]pyridine-5-carboxylate,
Phenethyl 4,7-dihydro-6-methyl-4-(3-nitrophenyl)-3-(4-chlorophenyl)thieno[2,3-b]pyridine-5-carboxylate,
Methyl 4,7-dihydro-6-methyl-4-(3-nitrophenyl)-3-(3,4-dimetoxyphenyl)thieno[2,3-b]pyridine-5-carboxylate,
Methyl 4,7-dihydro-6-methyl-4-(3-nitrophenyl)-3-methylthieno[2,3-b]pyridine-5-carboxylate,
Methyl 4,7-dihydro-6-methyl-4-(3-nitrophenyl)-3-n-butylthieno[2,3-b]pyridine-5-carboxylate,
Isopropyl 4,7-dihydro-6-methyl-4-(3-nitrophenyl)-3-n-butylthieno[2,3-b]pyridine-5-carboxylate,
Methoxyethyl 4,7-dihydro-6-methyl-4-(3-nitrophenyl)-3-n-butylthieno[2,3-b]pyridine-5-carboxylate,
Methyl 4,7-dihydro-6-methyl-4-(3-nitrophenyl)-3-isobutylthieno[2,3-b]pyridine-5-carboxylate,
Isopropyl 4,7-dihydro-6-methyl-4-(3-nitrophenyl)-3-isobutylthieno[2,3-b]pyridine-5-carboxylate,
Methoxyethyl 4,7-dihydro-6-methyl-4-(3-nitrophenyl)-3-isobutylthieno[2,3-b]pyridine-5-carboxylate,
Phenetyl 4,7-dihydro-6-methyl-4-(3-nitrophenyl)-3-isobutylthieno[2,3-b]pyridine-5-carboxylate,
Methyl 4,7-dihydro-6-methyl-4-(3-nitrophenyl)-3-(cyclopentylmethyl)thieno[2,3-b]pyridine-5-carboxylate,
Methyl 4,7-dihydro-6-methyl-4-(3-nitrophenyl)-3-(cyclohexylmethyl)thieno[2,3-b]pyridine-5-carboxylate,
Methyl 4,7-dihydro-6-methyl-4-(3-nitrophenyl)-3-cyclohexylthieno[2,3-b]pyridine-5-carboxylate,
Methyl 4,7-dihydro-6-methyl-4-(3-nitrophenyl)-3-phenyl-2-methylthieno[2,3-b]pyridine-5-carboxylate,
Methyl 4,7-dihydro-6-methyl-4-(3-nitrophenyl)-2-methylthieno[2,3-b]pyridine-5-carboxylate,
Methyl 4,7-dihydro-6-methyl-4-(3-nitrophenyl)-2,3-dimethylthieno[2,3-b]pyridine-5-carboxylate,
Methyl 4,7-dihydro-6-methyl-4-(3-nitrophenyl)-3-cyclopentylmethyl-2-methylthieno[2,3-b]pyridine-5-carboxylate,
Methyl 4,7-dihydro-6-methyl-4-(3-nitrophenyl)-2-isopropylthieno[2,3-b]pyridine-5-carboxylate,
Methyl 4,7-dihydro-6-methyl-4-(3-nitrophenyl)-3-n-butyl-2-n-propylthieno[2,3-b]pyridine-5-carboxylate,
Methyl 4,7-dihydro-6-methyl-4-(3-nitrophenyl)-2-ethoxycarbonyl-3-methylthieno[2,3-b]pyridine-5-carboxylate,
Methyl 4,7-dihydro-6-methyl-4-(3-nitrophenyl)-2,3-tetramethylenethieno[2,3-b]pyridine-5-carboxylate,
Methyl 4,7-dihydro-6-methyl-4-(2-nitrophenyl)-2-isopropylthieno[2,3-b]pyridine-5-carboxylate,
Methyl 4,7-dihydro-6-methyl-4-(2-nitrophenyl)-3-n-butyl-2-n-propylthieno[2,3-b]pyridine-5-carboxylate, and
Methyl 4,7-dihydro-6-methyl-4-(3-nitrophenyl)-3-isopropylthieno[2,3-b]pyridine-5-carboxylate.

Effect of the Invention

The compounds of the present invention are characterized by showing excellent antihypertensive and coronary vasodilating effects dependent on their Ca-blocking action with no systole inhibitory action which is one of the adverse reactions regarded as a defect of the conventional Ca-blockers. The biological tests on the following compounds were performed in the manner as explained below. Numbers by which the compounds are identified correspond to Example numbers.

Compound Tested

Reference Compound (R): Nifedipine
Compounds of the Invention:
1. Methyl 4,7-dihydro-6-methyl-4-(3-nitrophenyl)-3-phenylthieno[2,3-b]pyridine-5-carboxylate,
7. Methyl 4,7-dihydro-6-methyl-4-(3-nitrophenyl)-3-n-butylthieno[2,3-b]pyridine-5-carboxylate,
10. Methyl 4,7-dihydro-6-methyl-4-(3-nitrophenyl)-3-isobutylthieno[2,3-b]pyridine-5carboxylate,
12. Methoxyethyl 4,7-dihydro-6-methyl-4-(3-nitrophenyl)-3-isobutylthieno[2,3-b]pyridine-5-carboxylate, 16. Methyl 4,7-dihydro-6-methyl-4-(3-nitrophenyl)-3-cyclohexylthieno[2,3-b]pyridine-5-carboxylate,
19. Methyl 4,7-dihydro-6-methyl-4-(3-nitrophenyl)-2,3-dimethylthieno[2,3-b]pyridine-5-carboxylate, and
23. Methyl 4,7-dihydro-6-methyl-4-(3-nitrophenyl)-2-ethoxycarbonyl-3-methylthieno[2,3-b]pyridine-5-carboxylate.

Test Method (1) Antihypertensive Action:

Female Spontaneously Hypertensive Rats (hereinafter referred to as SHR) with 160 mmHg of systolic pressure were employed without anaesthetization. The systolic pressure after SHRs were warmed at 50° C. for 2–3 minutes was bloodlessly measured by the tail-cuff method [Japan J. Pharmacol., 28, 617 (1978)] using a Physiograph and an Electrosphygmomanometer (DMP-4B, PE-300, Narco Biosystems, Inc., Houston). Each compound was intraperitoneally administered to SHR at a dose of 3 mg per kilogram.

(2) Coronary Vasodilating Action and Systole Inhibitory Action:

Guinea pigs with 400–800 g of body weight were strongly hit on their heads and the cartoid artery of each Guinea pigs was cut down in order to make them bloodless. The heart was isolated and perfused with a constant pressure (50 cm $H_2O$) by the Langendorff method [Basic Pharmacology & Therapeutics, 9(4), 181 (1981)]. Krebs-Ringer bicarbonate solution (27° C.) containing 0.5% defibrinated blood was employed as a perfusate, into which a mixture of 95% oxygen with 5% carbon dioxide was continuously introduced. The flowing perfusate was led into a drop counter, and the changes of the flow i.e. increase and decrease are regarded as the respective indications for coronary vasodilation and vasoconstriction. The isomeric contraction of apex and the number of drops of the coronary perfusate were recorded on a Recticorder (RJG 3006, Nihon Koden) by way of an F-D Pick-up (SB-1T, Nihon Koden). Each of the test compounds at a dose of 0.1 μg was administered through a short rubber tube connected to the aorta and the cannula.

Results

Antihypertensive action is shown in a maximal decrease of blood pressure, i.e., a maximum difference between systolic pressures after and before the administration of the test compound.

Coronary vasodilating action is shown in changes of the quantity of the perfusate, and the duration of the action is shown in the time during which the increase (over 20%) in the quantity of the perfusate was observed.

TABLE 1
Antihypertensive action and Coronary vasodilating action and the duration of effect.

| Compounds | Maximum Decrease of BP (mmHg) | Change in Perfusate (%) | Duration (min.) |
|---|---|---|---|
| 1 | 14 | 42.6 | 10 |
| 7 | 54 | 45.2 | >60 |
| 10 | 34 | 53.1 | >60 |
| 12 | 39 | 49.8 | >60 |
| 16 | 57 | 49.4 | >30 |
| 19 | 0 | 21.6 | — |
| 23 | 32 | 0 | — |
| R | 45 | 38.0 | 5 |

Since the compounds of this invention, as clearly seen from the above-listed results, show the high antihypertensive and coronary vasodilating actions, they can be used in humans or animals as cardiovascular agents with lesser adverse reactions.

The compounds of this invention can be orally or pareterally administered to human or animals and formed into various type of formulations in compliance with the usage. They, for instance, can be tablets, capsules, pills, granules, fine granules, aqueous solutions, emulsions or the like. In the course of the formulation, conventional carriers or diluents such as lactose, sucrose, starch, cellulose, talc, magnesium stearate, magnesium oxide, calcium sulfate, powdered gum arabic, gelatin, sodium alginate, sodium benzoate, stearic acid and the like are employed. Injections may be used in a form of a solution in distilled water, saline, Ringer's solution of the like, or a suspension in sesame oil.

The compounds of this invention may be administered to an adult orally at a dose of about 1–50 mg a day, or intravenously at about 0.5–20 mg a day.

EXAMPLE 1

Preparation of methyl 4,7-dihydro-6-methyl-4-(3-nitrophenyl)-3-phenylthieno[2,3-b]pyridine-5-carboxylate (1)

Method A

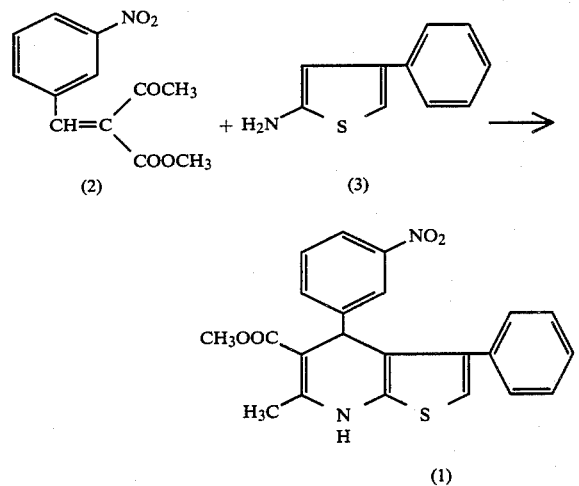

In 10 ml of t-butanol are dissolved 1.42 g (5.71 mmol) of methyl 3-nitrobenzylideneacetoacetate (2) and 1.0 g (5.71 mmol) of 5-amino-3-phenylthiophene (3) and the solution is stirred at 80° C. for 4 hours. The reaction mixture is then evaporated to give a residue, which is chromatographed on a silica gel column with benzene/ethyl acetate (9/1) as an eluent to give 0.254 g (yield 10.9%) of the titled compound (1). This is recrystallized from methanol to give yellow plates, mp. 213°–215° C.

Elementary Analysis: Calcd. (%) for $C_{22}H_{18}N_2O_4S$: C, 65.01; H, 4.46; N, 6.89, Found (%): C, 64.83; H, 4.34; N, 6.93.

IR(Nujol) νmax: 3300, 1632, 1350 $cm^{-1}$.

NMR($CDCl_3$) δppm: 2.45, 3.58(s, 3H×2), 5.35(s, 1H), 6.48(s, 1H), 6.48(NH), 6.85–8.00(m, 9H).

Method B

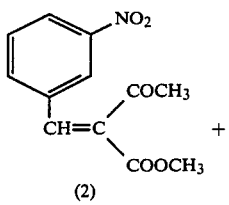

(2)

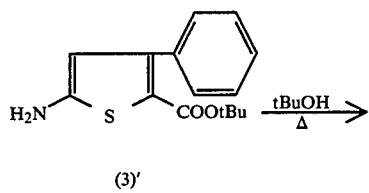

(3)'

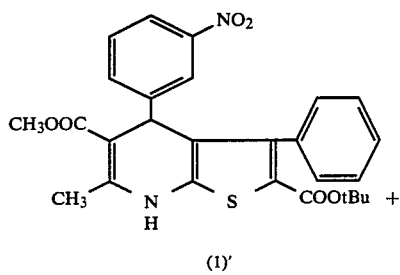

(1)'

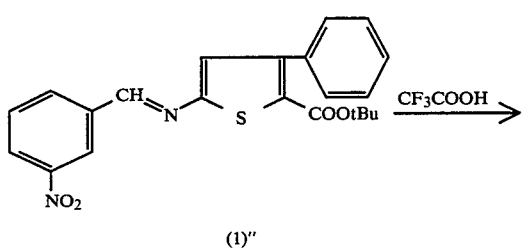

(1)''

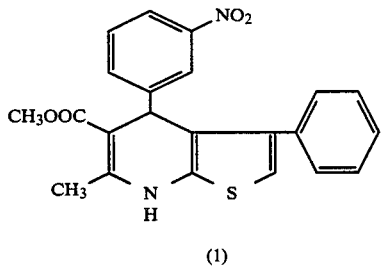

(1)

In the sequence, tBu represents tertiary butyl.

A solution of 0.18 g (0.73 mmol) of methyl 3-nitrobenzylideneacetoacetate (2) and 0.20 g (0.73 mmol) of t-butyl 5-amino-3-phenylthiophene-2-carboxylate (3)' dissolved in 2 ml of t-butanol is degassed and stirred at 90° C. for 95 hours under nitrogen atmosphere, then evaporated to give a residue. The residue is chromatographed on a silica gel column to give 33 mg (yield 11.1%) of the Schiff's base (1)'' as an ethylene chloride fraction and subsequently 0.268 g (yield 73.4%, yellow amorphous) of 2-t-butoxycarbonyl derivative (1)' of the objective compound (1) as a methylene chloride/acetonitrile (9/1) fraction.

NMR(CDCl$_3$) δppm: 1.81 (s, 9H), 2.38, 3.53 (s, 3H×2), 5.00 (s, 1H), 6.82~7.95 (m, 9H), 8.07 (NH).

A solution of 0.268 g (0.53 mmol) of the derivative (1)' dissolved in 2 ml of trifluoroacetic acid is stirred at 20° C. for about an hour and evaporated in vacuo to give a residue, to which ice and water are added. The mixture is alkalized with aqueous sodium hydrogen carbonate and extracted with methylene chloride. The organic layer is dried over magnesium sulfate, filtered, and evaporated to give a residue, which is chromatographed on a silica gel column (with methylene chloride as an eluent) to give 0.174 g (yield 80.2%) of the titled compound (1).

EXAMPLE 2–27

Method A

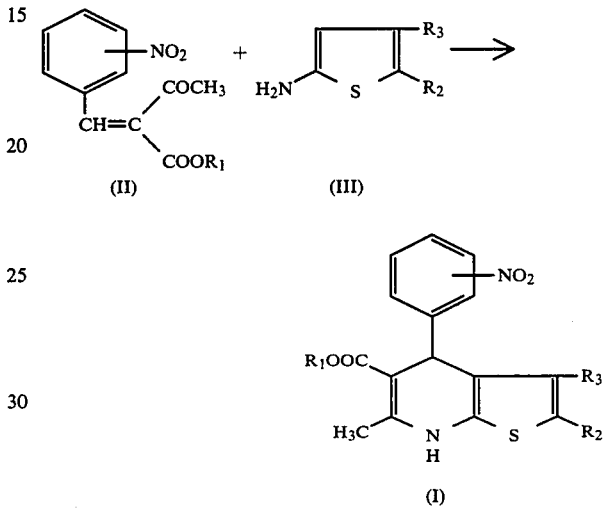

In the sequence, $R^1$, $R^2$, and $R^3$ each is the same as above.

In a solvent are dissolved compounds (II) and (III) and the solution is, if required under nitrogen atmosphere, allowed to react at room temperature or under heating. The reaction mixture is evaporated in vacuo to give a residue, which is either recrystallized from methanol or tetrahydrofuran (THF)/methanol or chromatographed on a silica gel column to give an objective compound (I). This may be further refined by recrystallization.

Method B

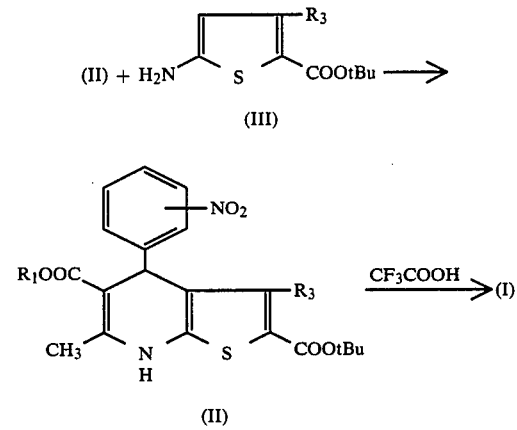

In the sequence, $R^1$, $R^2$, and $R^3$ each is the same as above.

In a solvent are dissolved compounds (II) and (III)' and the solution is, under nitrogen atmosphere, allowed to react at room temperature or under heating. The reaction mixture is evaporated in vacuo to give a residue, which is chromatographed on a silica gel column to give an objective compound (I)'. The compound (I)' is reacted with trifluoroacetic acid under cooling or at room temperature and the reaction mixture evaporated in vacuo to give a residue, to which ice and water are added. The mixture is alkalized with a base then extracted with a solvent. The organic layer is dried and evaporated in vacuo to give a residue, which is chromatographed on a silica gel column to give an objective compound (I). This may be further refined by recrystallization.

Compounds of the present invention can be prepared according to the method A or B.

The compounds of the present invention prepared in Examples 1–27 and details of the reaction conditions are shown in Tables 2 and 3, respectively. Further, Table 4 shows recrystallization solvents for the products or the acid addition salts, and appearance (crystal form, color), molecular formulae, and the elementary analysis data of the compounds; and Table 5 shows IR and NMR data on each compound.

TABLE 2
(No. 1)

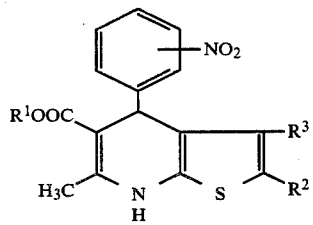

| Exam. No. | $R^1$ | $R^2$ | $R^3$ | Postn. of $-NO_2$ |
|---|---|---|---|---|
| 1 | $-CH_3$ | H | $-C_6H_5$ | 3 |
| 2 | $\sim\!\!\sim\!C_6H_5$ | H | $-C_6H_5$ | " |
| 3 | $-CH_3$ | H | $-\!\!\langle\ \rangle\!\!-Cl$ | " |
| 4 | $\sim\!\!\sim\!C_6H_5$ | H | $-\!\!\langle\ \rangle\!\!-Cl$ | " |

TABLE 2-continued
(No. 1)

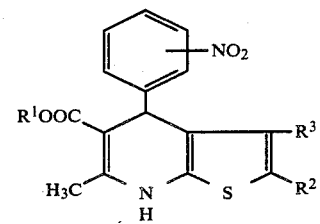

| Exam. No. | $R^1$ | $R^2$ | $R^3$ | Postn. of $-NO_2$ |
|---|---|---|---|---|
| 5 | $-CH_3$ | H | $-\!\!\langle\ \rangle\!\!-OCH_3$ (OCH_3) | " |
| 6 | $-CH_3$ | H | $-CH_3$ | " |
| 7 | $-CH_3$ | H | $-n-C_4H_9$ | " |
| 8 | $-isoC_3H_7$ | H | $-n-C_4H_9$ | " |
| 9 | $\sim\!\!\sim\!OCH_3$ | H | $-n-C_4H_9$ | " |
| 10 | $-CH_3$ | H | $-iso-C_4H_9$ | " |
| 11 | $-isoC_3H_7$ | H | $-iso-C_4H_9$ | " |
| 12 | $\sim\!\!\sim\!OCH_3$ | H | $-iso-C_4H_9$ | " |
| 13 | $\sim\!\!\sim\!C_6H_5$ | H | $-iso-C_4H_9$ | " |
| 14 | $-CH_3$ | H | cyclopentylmethyl | " |
| 15 | $-CH_3$ | H | cyclohexylmethyl | " |
| 16 | $-CH_3$ | H | cyclohexyl | " |
| 17 | $-CH_3$ | $-CH_3$ | $-C_6H_5$ | " |
| 18 | $-CH_3$ | $-CH_3$ | H | " |
| 19 | $-CH_3$ | $-CH_3$ | $-CH_3$ | " |
| 20 | $-CH_3$ | $-CH_3$ | cyclopentylmethyl | " |
| 21 | $-CH_3$ | $isoC_3H_7$ | H | " |
| 22 | $-CH_3$ | $n-C_3H_7$ | $n-C_4H_9$ | " |
| 23 | $-CH_3$ | $COOC_2H_5$ | $CH_3$ | " |
| 24 | $-CH_3$ | $-(CH_2)_4-$ | | " |
| 25 | $-CH_3$ | $isoC_3H_7$ | M | 2 |
| 26 | $-CH_3$ | $n-C_3H_7$ | $n-C_4H_9$ | " |
| 27 | $-CH_3$ | H | $-iso-C_3H_7$ | 3 |

TABLE 3

| | Amount Used, g (mmol) | | | Conditions | | Amount of Comd. I Used | | Conditions | | | |
|---|---|---|---|---|---|---|---|---|---|---|---|
| Exam. No. | Compound II | Compound III or III' | Solvent (ml) | Temp (°C.) | Time (hr) | g (mmol) | $CF_3COOH$ (ml) | Temp (°C.) | Time (hr) | Method | Yield (%) |
| 1 | 1.42(5.72) | 1.00(5.71) | t-butanol (10) | 80 | 4 | 0.27 | 2 | 20 | 1 | A | 10.9 |
| | 0.18(0.73) | 0.20(0.73) | (2) | 90 | 95 | | | | | B | 58.9 |
| 2 | 0.49(1.44) | 0.40(1.44) | t-butanol (5) | 90 | 65 | 0.48(0.80) | 4 | 20 | 1 | B | 50.4 |
| 3 | 0.40(1.61) | 0.50(1.61) | t-butanol (5) | 90 | 70 | 0.59(1.09) | 3 | 20 | 1 | B | 62.6 |
| 4 | 0.60(1.76) | 0.54(1.76) | t-butanol (5) | 90 | 73 | 0.59(0.94) | 3 | 20 | 1 | B | 44.1 |
| 5 | 0.17(0.68) | 0.23(0.68) | t-butanol (3) | 90 | 95 | 0.26(0.46) | 2 | 20 | 1 | B | 63.2 |
| 6 | 2.31(9.27) | 1.05(9.27) | t-butanol (10) | 80 | 3 | 0.5 (1.13) | 2 | 20 | 2 | A | 9.7 |
| | 3.86(15) | 3.30(15) | (30) | 90 | 140 | | | | | B | 55.1 |
| 7 | 0.50(2.0) | 0.5(2.0) | t-butanol (5) | 90 | 70 | 0.59(1.21) | 2.5 | 20 | 1 | B | 55.9 |

TABLE 3-continued

| Exam. No. | Amount Used, g (mmol) Compound II | Amount Used, g (mmol) Compound III or III | Solvent (ml) | Conditions Temp (°C.) | Conditions Time (hr) | Amount of Comd. I Used g (mmol) | CF₃COOH (ml) | Conditions Temp (°C.) | Conditions Time (hr) | Method | Yield (%) |
|---|---|---|---|---|---|---|---|---|---|---|---|
| 8 | 0.39(1.41) | 0.36(1.41) | t-butanol (4) | 90 | 67 | 0.47(0.91) | 2 | 20 | 1 | B | 57.3 |
| 9 | 0.55(1.88) | 0.48(1.88) | t-butanol (5) | 90 | 72 | 0.57(1.07) | 2.5 | 20 | 1 | B | 49.8 |
| 10 | 0.34(1.37) | 0.35(1.37) | t-butanol (4) | 90 | 65 | 0.42(0.87) | 4 | 20 | 1 | B | 59.7 |
| 11 | 0.389(1.4) | 0.358(1.4) | t-butanol (4) | 90 | 64 | 0.5 (0.96) | 2 | 20 | 1 | B | 62.0 |
| 12 | 0.49(1.65) | 0.40(1.57) | t-butanol (4) | 90 | 63 | 0.5 (0.95) | 3 | 20 | 1 | B | 56.7 |
| 13 | 0.47(1.37) | 0.35(1.37) | t-butanol (5) | 90 | 90 | 0.46(0.79) | 4 | 20 | 1 | B | 51.3 |
| 14 | 1.58(6.32) | 1.78(6.32) | t-butanol (16) | 90 | 100 | 1.98(3.87) | 15 | 20 | 1 | B | 51.0 |
| 15 | 0.46(1.85) | 0.55(1.85) | t-butanol (5) | 90 | 113 | 0.61(1.15) | 2 | 20 | 1 | B | 48.9 |
| 16 | 1.38(5.52) | 1.00(5.52) | t-butanol (10) | 80 | 3 | | | | | A | 13.3 |
| 17 | 0.66(2.65) | 0.50(2.64) | t-butanol (4) | 80 | 3 | | | | | A | 49.7 |
| 18 | 0.66(2.65) | 0.30(2.65) | t-butanol (4) | 80 | 3 | | | | | A | 59.6 |
| 19 | 1.37(5.50) | 0.70(5.50) | t-butanol (10) | 80 | 3 | | | | | A | 58.8 |
| 20 | 0.38(1.54) | 0.30(1.54) | t-butanol (4) | 90 | 5 | | | | | A | 24.7 |
| 21 | 0.87(3.50) | 0.50(3.50) | t-butanol (6) | 80 | 3 | | | | | A | 61.4 |
| 22 | 0.82(3.29) | 0.65(3.29) | t-butanol (6) | 80 | 3 | | | | | A | 39.6 |
| 23 | 2.50(10.0) | 1.94(10.5) | t-butanol (20) | 85 | 90 | | | | | A | 78.5 |
| 24 | 0.91(3.64) | 0.56(3.64) | t-butanol (10) | 50 | 3 | | | | | A | 69.5 |
| 25 | 0.87(3.50) | 0.50(3.50) | t-butanol (6) | 80 | 3 | | | | | A | 55.8 |
| 26 | 0.63(2.53) | 0.50(2.53) | t-butanol (7) | 80 | 5 | | | | | A | 18.3 |
| 27 | 0.74(2.97) | 0.72(2.97) | t-butanol (7) | 90 | 43 | 0.05(0.11) | 0.3 | 20 | 1 | B | 2.0 |

TABLE 4

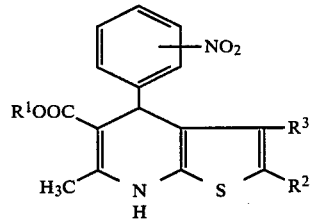

| Exam. No. | Appearance | Solvent for Recrystallization | mp. (°C.) | Molecular Formula | Elementary Analysis (%) Calculated C | H | N | Found C | H | N |
|---|---|---|---|---|---|---|---|---|---|---|
| 1 | YP1 | methanol | 213–215 | $C_{22}H_{18}N_2O_4S$ | 65.01 | 4.46 | 6.89 | 64.83 | 4.34 | 6.93 |
| 2 | YP1 | ethanol | 147–150 | $C_{29}H_{24}N_2O_4S$ | 70.14 | 4.87 | 5.64 | 70.20 | 4.91 | 5.68 |
| 3 | YP1 | THF/ethanol | 229–231 | $C_{22}H_{17}ClN_2O_4S$ | 59.95 | 3.89 | 6.35 | 59.92 | 4.17 | 6.30 |
| 4 | YP1 | ethanol | 169–170 | $C_{29}H_{23}ClN_2O_4S$ | 65.59 | 4.37 | 5.28 | 65.44 | 4.53 | 5.19 |
| 5 | YP1 | THF/methanol | 220–222 | $C_{24}H_{22}N_2O_6S$ | 61.79 | 4.75 | 6.00 | 61.56 | 4.67 | 5.85 |
| 6 | YP1 | methanol | 205–208 | $C_{17}H_{16}N_2O_4S$ | 59.29 | 4.68 | 8.13 | 59.24 | 4.57 | 8.10 |
| 7 | YP | methanol | 155–156 | $C_{20}H_{22}N_2O_4S$ | 62.16 | 5.74 | 7.25 | 61.92 | 5.73 | 7.26 |
| 8 | YN | diisopropyl ether | 116–117 | $C_{22}H_{26}N_2O_4S$ | 63.75 | 6.32 | 6.76 | 63.71 | 6.38 | 6.78 |
| 9 | YP | diisopropyl ether | 134–136 | $C_{22}H_{26}N_2O_5S$ | 61.38 | 6.09 | 6.51 | 61.41 | 6.18 | 6.54 |
| 10 | YN | methanol | 189–190 | $C_{20}H_{22}N_2O_4S$ | 62.16 | 5.74 | 7.25 | 61.97 | 5.54 | 7.30 |
| 11 | YP | diisopropyl ether | 80–84 | $C_{22}H_{25}N_2O_4S \cdot \frac{1}{2}iPr_2O$ | 64.63 | 6.94 | 6.03 | 64.62 | 7.00 | 6.00 |
| 12 | YP | diisopropyl ether | 128–130 | $C_{22}H_{25}N_2O_6S$ | 61.52 | 5.87 | 6.52 | 61.43 | 6.10 | 6.50 |
| 13 | YP | diisopropyl ether | 125–127 | $C_{27}H_{28}N_2O_4S$ | 68.04 | 5.92 | 5.88 | 68.15 | 5.81 | 5.95 |
| 14 | YP | methanol | 166–168 | $C_{22}H_{24}N_2O_4S$ | 64.06 | 5.86 | 6.79 | 63.87 | 5.94 | 6.71 |
| 15 | YN | methanol | 163–166 | $C_{23}H_{26}N_2O_4S$ | 64.77 | 6.14 | 6.57 | 64.73 | 6.00 | 6.37 |
| 16 | YP1 | diisopropyl ether | 180–182 | $C_{22}H_{24}N_2O_4S$ | 64.06 | 5.86 | 6.79 | 64.07 | 5.80 | 6.73 |
| 17 | YP | THF/methanol | 196–197 | $C_{23}H_{20}N_2O_4S$ | 65.70 | 4.79 | 6.66 | 65.55 | 4.66 | 6.89 |
| 18 | YP | THF/methanol | 212–215 | $C_{17}H_{16}N_2O_4S$ | 59.29 | 4.68 | 8.13 | 59.18 | 4.57 | 8.15 |
| 19 | YP | THF | 250–252 | $C_{18}H_{18}N_2O_4S$ | 60.32 | 5.06 | 7.82 | 60.46 | 4.96 | 7.67 |
| 20 | YP1 | ethanol | 184–186 | $C_{23}H_{26}N_2O_4S$ | 64.77 | 6.14 | 6.57 | 64.66 | 6.17 | 6.60 |
| 21 | YP | diisopropyl ether n-hexane | 132–134 | $C_{19}H_{20}N_2O_4S$ | 61.28 | 5.41 | 7.52 | 61.29 | 5.46 | 7.49 |
| 22 | YP | ethanol | 150–152 | $C_{23}H_{28}N_2O_4S$ | 64.46 | 6.59 | 6.54 | 64.21 | 6.29 | 6.48 |
| 23 | YP | methanol | 206–208 | $C_{20}H_{20}N_2O_6S$ | 57.69 | 4.84 | 6.73 | 57.49 | 4.72 | 6.64 |
| 24 | YP1 | THF/methanol | 231–233 | $C_{20}H_{20}N_2O_4S$ | 62.48 | 5.24 | 7.29 | 62.54 | 5.20 | 7.32 |
| 25 | YP | diisopropyl ether n-hexane | 105–109 | $C_{19}H_{20}N_2O_4S$ | 61.28 | 5.41 | 7.52 | 60.87 | 5.37 | 7.33 |
| 26 | Oil | | | | | | | | | |
| 27 | YP1 | methanol | 193–195 | $C_{19}H_{20}N_2O_4S$ | 61.28 | 5.41 | 7.52 | 61.06 | 5.43 | 7.38 |

(NOTE)
YP1: Yellow Plates, YP: Yellow Prism, YN: Yellow needles.

TABLE 5

| Exam. No. | IR(Nujol)$v_{max}^{cm-1}$ NH | CO | NO$_2$ | NMR(CDCl$_3$)δ |
|---|---|---|---|---|
| 1 | 3300 | 1632 | 1350 | 2.45,3.58(s,3H × 2),5.35(s,1H),6.48(s,1H),6.48(NH),6.85~8.00(m,9H) |
| 2 | 3305 | 1628 | 1345 | 2.36(s,3H),2.82(t,2H),4.22(m,2H),5.29(s,1H),6.47(s,1H),6.63(NH),6.90~7.90(m,14H) |
| 3 | 3290 | 1627 | 1350 | 2.43,3.60(s,6H),5.31(s,1H),6.50(s,1H),6.57(NH),6.93~8.00(m,8H) |
| 4 | 3285 | 1623 | 1340 | 2.37(s,3H),2.85(t,2H),4.27(m,2H),5.22(s,1H),6.48(s,1H),6.67(NH),6.88~7.95(m,13H) |
| 5 | 3350 | 1648 | 1353 | 2.45,3.62,3.72,3.91(s,3H × 4),5.37(s,1H),6.50(s,1H),6.73(NH),6.50~8.00(m,7H) |
| 6 | 3290 | 1640 | 1350 | 1.88,2.40,3.62(s,3H × 3),5.22(s,1H),6.22(s,1H),6.45(NH),7.17~8.13(4m,4H) |
| 7 | 3305 | 1630 | 1345 | 0.67~2.33(m,9H),2.40,3.65(s,3H × 2),5.27(s,1H),6.23(s,1H),6.55(NH),7.27~8.13(m,4H) |
| 8 | 3300 | 1627 | 1341 | 0.63~2.33(m,9H),1.20(d,6H),2.40(s,3H),5.00(m,1H),5.27(s,1H),6.23(s,1H),6.47(NH),7.27~8.17(m,4H) |
| 9 | 3280 | 1627 | 1339 | 0.67~2.33(m,9H),2.38,3.35(s,3H × 2),3.55(t,2H),4.18(t,2H),5.27(s,1H),6.22(s,1H),6.53(NH),7.23~8.13(m,4H) |
| 10 | 3300 | 1636 | 1340 | 0.78(d,6H),1.60(m,1H),2.07(d,2H),2.37,3.63(s,3H × 2),5.25(s,1H),6.22(s,1H),6.53(NH),7.23~8.10(m,4H) |
| 11 | 3260 | 1620 | 1350 | 0.79(d,6H),1.20(d,6H),1.60(m,1H),2.08(d,2H),2.38(s,3H),4.98(m,1H),5.26(s,1H),6.20(s,1H),6.86(NH),7.25~8.17(m,4H) |
| 12 | 3315 | 1635 | 1350 | 0.78(d,6H),1.58(m,1H),2.08(d,2H),2.39,3.38(s,3H × 2),3.60(m,2H),4.22(m,2H),5.30(s,1H),6.22(s,1H),6.94(NH),7.28~8.17(m,4H) |
| 13 | 3325 | 1640 | 1341 | 0.79(s,6H),1.57(m,1H),2.03(d,2H),2.32(s,3H),2.93(t,2H),4.30(m,2H),5.15(s,1H),6.20(s,1H),6.52(NH),7.00~8.03(m,9H) |
| 14 | 3315 | 1633 | 1348 | 0.73~2.32(m,11H),2.38,3.66(s,3H × 2),5.27(s,1H),6.24(s,1H),6.62(NH),7.25~8.13(m,4H) |
| 15 | 3315 | 1630 | 1340 | 0.43~1.75(m,11H),2.09(d,2H),2.38,3.67(s,3H × 2),5.27(s,1H),6.20(s,1H),6.77(NH),7.28~8.13(m,4H) |
| 16 | 3310 | 1630 | 1340 | 0.73~2.57(m,11H),2.40,3.67(s,3H × 2),5.31(s,1H),6.22(s,1H),6.70(NH),7.17~8.13(m,4H) |
| 17 | 3335 | 1662 | 1338 | 2.10,2.41,3.50(s,3H × 3),5.07(s,1H),6.52(NH),6.70~7.93(m,9H) |
| 18 | 3275 | 1632 | 1340 | 2.26(d,3H),2.42,3.55(s,3H × 2),5.25(s,1H),6.13(q,1H),6.48(NH),7.23~8.16(m,4H) |
| 19 | 3280 | 1628 | 1338 | 1.72,2.13,2.28,3.48(s,3H × 4),5.09(s,1H),9.63(NH),7.41~8.07(m,4H) |
| 20 | 3345 | 1685 | 1348 | 0.73~2.27(m,11H),2.20,2.35,3.65(s,3H × 3),5.23(s,1H),6.47(NH),7.23~8.10(m,4H) |
| 21 | 3300 | 1630 | 1350 | 1.20(d,6H),2.43,3.58(s,3H × 2),2.95(m,1H),5.28(s,1H),6.18(s,1H),6.45(NH),7.23~8.15(m,4H) |
| 22 | 3300 | 1632 | 1345 | 0.62~1.78(m,12H),2.35(m,4H),2.36,3.63(s,3H × 2),5.22(s,1H),6.55(NH),7.17~8.13(m,4H) |
| 23 | | | | 1.31(t,3H),2.06,2.42,3.64(s,3H × 3),4.24(q,2H),5.19(s,1H),7.13~8.03(m,5H) |
| 24 | 3310 | 1640 | 1350 | 1.43~2.73(m,8H),2.38,3.58(s,3H × 2),5.13(s,1H),6.42(NH),7.17~8.13(m,4H) |
| 25 | 3400 | 1690 | 1350 | 1.22(d,6H),2.42,3.45(s,3H × 2),2.97(m,1H),5.67(s,1H),6.48(s,1H),6.32(NH),7.39(m,4H) |
| 26 | 3430 | 1690 | 1356 | 0.55~1.90(m,12H),2.43(m,4H),2.28,3.50(s,3H × 2),5.93(s,1H),6.68(NH),7.02~7.77(m,4H) |
| 27 | 3285 | 1639 | 1338 | 0.96(d,6H),2.38,3.67(s,3H × 2),2.61(m,1H),5.33(s,1H),6.29(s,1H),6.63(NH),7.28~8.13(m,4H) |

REFERENCE PREPARATION 1

Production of t-butyl phenyl-5-aminothiophene-2-carboxylate (3)'

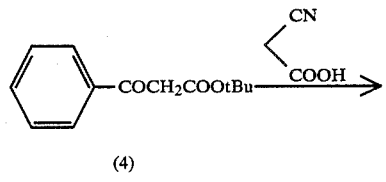

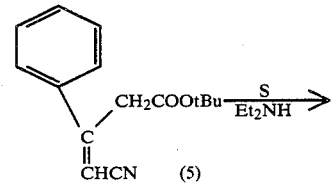

-continued

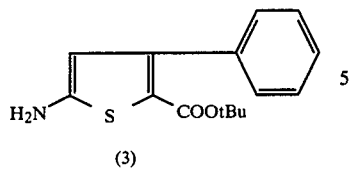

(3)

wherein tBu is the same as defined above, and Et represents ethyl.

A mixture of 3.28 g (14.9 mmol) of t-butyl benzoylacetate (4), 1.3 g (15.3 mmol) of cyanoacetic acid, and 0.3 g of ammonium acetate with 0.1 ml of piperidine and 15 ml of t-butanol is refluxed under heating for 110 hours. The reaction mixture is evaporated to leave a residue, which is dissolved in ethyl ether, washed with dil. aqueous solution of sodium hydrogencarbonate, and dried over magnesium sulfate. The ethyl ether is removed to leave a residue, which is distilled in vacuo to give 1.52 g (yield 42.0%: as a mixture of Z- and E-forms) of 3-phenyl-4-cyano-3-butenoate (5), bp. 126° C. (0.1 mmHg).

To a suspension of 1.48 g (6.1 mmol) of the compound (5) and 0.2 g (6.1 mmol) of sulfur in 5 ml of ethanol is dropwise added 1 ml of diethylamine while being stirred at room temperature, and the reaction mixture is further stirred overnight. The mixture is evaporated to leave a residue, which is chromatographed on a silica gel column with methylene chloride as an eluent to give 1.03 g (yield 61.3%) of the titled compound (3)', mp. 110°–116° C.

IR(CHCl₃) νmax: 3475, 3390, 1665 cm⁻¹.
NMR(CDCl₃) δppm: 1.34 (s, 9H), 4.22 (NH₂), 6.03 (s, 1H), 7.37 (m, 5H).

REFERENCE PREPARATIONS 2–9

General Procedure

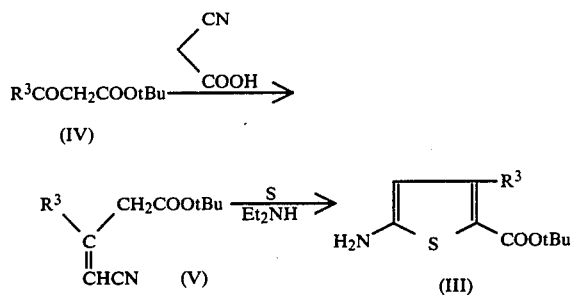

A solution of a compound (IV) and cyanoacetic acid dissolved in a solvent is reacted at room temperature or under heating to give a compound (V). To a suspension or a solution of the compound (V) and sulfur in a solvent is added diethylamine, and the mixture is stirred. The mixture is evaporated to leave a reisue, which is either chromatographed on a silica gel column or crystallized from a solvent to give the objective compound (III)'. This may be employed in the next reaction step without purification.

According to the general procedure as above, the following starting materials (Reference Preparations 2–9) are obtained (Table 6).

TABLE 6

$$R^3COCH_2COOtBu + \begin{array}{c} CN \\ < \\ COOH \end{array} \longrightarrow \begin{array}{c} R^3 \\ \diagdown \\ \end{array} \begin{array}{c} COOtBu \\ CN \end{array}$$

(IV)         (V)

| Reference Preparation | R³ | Amount Used, g(mmol) | | | | Solvent (ml) | Reaction Conditions | |
|---|---|---|---|---|---|---|---|---|
| | | IV | CN<COCH | AcONH₄ | HN(piperidine) | | Temp. (°C.) | Time (hr) |
| 2 | 4-Cl-C₆H₄– | 4.4(17) | 1.6(19) | — | 0.1 | t-butanol (20) | Reflux | 99 |
| 3 | 3,4-(CMe)₂-C₆H₃– | 0.4(1.3) | 0.3(2.6) | — | 0.03 | t-butanol (3) | " | 70 |
| 4 | CH₃ | 8.5(100) | 15.8(100) | 1.2 | 1.7 | toluene (100) | " | 6 |
| 5 | isoC₃H₇ | 3.7(20) | 1.7(20) | 0.3 | 0.1 | t-butanol (15) | " | 140 |
| 6 | nC₄H₉ | 11.6(58) | 5.1(60) | 1.2 | 0.5 | t-butanol (35) | " | 150 |
| 7 | isoC₄H₉ | 5.0(25) | 2.3(27) | 0.5 | 0.2 | t-butanol (15) | " | 110 |
| 8 | cyclopentyl-CH₂– | 3.0(13) | 1.2(14) | 0.25 | 0.1 | toluene (12) | " | 6 |

TABLE 6-continued

| 9 | 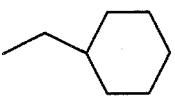 | 4.4(18) | 2.1(25) | 0.45 | 0.1 | toluene (16) | " | 11 |

$$\underset{(V)}{\overset{R^3}{\underset{CN}{\diagup}}\diagdown COOtBu} + S \xrightarrow{Et_2NH} \underset{(III)}{\overset{R^3}{\underset{H_2H}{\diagup S\diagdown}}COOtBu}$$

| Reference Preparation | R³ | Amount used, g(mmol) V | S | Et₂NH | Solvent (ml) | Conditions Temp. (°C.) | Time (hr) |
|---|---|---|---|---|---|---|---|
| 2 | 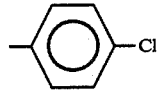 | 4.7 | 0.5(15.6) | 2.5 | ethanol (12) | 20 | 18 |
| 3 | 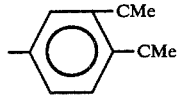 | 0.36 | 0.04(1.2) | 0.4 | ethanol (2) | 20 | 20 |
| 4 | CH₃ | 9.1(50) | 1.6(50) | 7.0 | ethanol (25) | 35 | 3 |
| 5 | isoC₃H₇ | 1.6(8) | 0.25(8) | 1.0 | ethanol (5) | 20 | 21 |
| 6 | nC₄H₉ | 7.8(35) | 1.3(35) | 2.0 | t-butanol (8) | 60 | 18 |
| 7 | isoC₄H₉ | 2.7(12) | 0.4(12) | 1.6 | ethanol (8) | 20 | 17 |
| 8 | 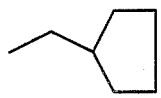 | 1.5 | 0.18(5.6) | 0.6 | ethanol (3) | 20 | 2 |
| 9 | 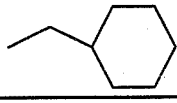 | 1.1(4.2) | 0.14(4.2) | 0.5 | ethanol (2.5) | 20 | 4 |

TABLE 7

| Preptn No. | R³ | % Yield (V) | bp °C. (mmHg) | % Yield of (III) | NMR (CDCl₃)δ |
|---|---|---|---|---|---|
| 2 | 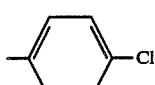 | — | | 53.4 | 1.39(s,9H), 4.23(NH₂), 6.00(s,1H), 9.32(s,4H) |
| 3 | 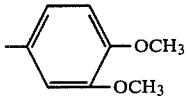 | — | | 52.8 | 1.38(s,9H), 3.87(s,6H), 4.27(NH₂), 6.04(s,1H), 6.79~7.07(m,3H) |
| 4 | CH₃ | 81.0 | 78(0.1) | 69.5 | 1.53(s,9H), 2.35(s,3H), 4.32(NH₂), 5.85(s,1H) |
| 5 | isoC₃H₇ | 39.0 | 88(0.1) | 78.8 | 1.16(d,6H), 1.52(s,9H), 3.80(m,1H), 4.15(NH₂), 6.04(s,1H) |
| 6 | nC₄H₉ | 60.0 | 90(0.1) | 70.2 | 0.80~1.80(m,7H), 1.52(s,9H), 2.80(t,2H), 4.13(NH₂), 5.93(s,1H) |
| 7 | isoC₄H₉ | 48.2 | 90(0.1) | 51.7 | 0.90(d,6H), 1.52(s,9H), 1.88(m,1H), 2.70(d,2H), 4.15(NH₂), 5.91(s,1H) |
| 8 |  | — | | 40.0 | 0.77~2.32(m,9H), 2.87(d,2H), 4.23(NH₂), 5.97(s,1H) |

TABLE 7-continued

| Preptn No. | R³ | % Yield (V) | bp °C. (mmHg) | % Yield of (III) | NMR (CDCl₃)δ |
|---|---|---|---|---|---|
| 9 | 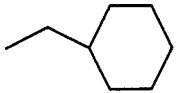 | 23.1 | 120(0.1) | 44.0 | 0.68~1.90(m,11H), 1.53(s,9H), 2.73(d,2H), 4.13(NH₂), 5.91(s,1H) |

REFERENCE PREPARATION 10

Production of 2-amino-5-isopropylthiophene (3-27)

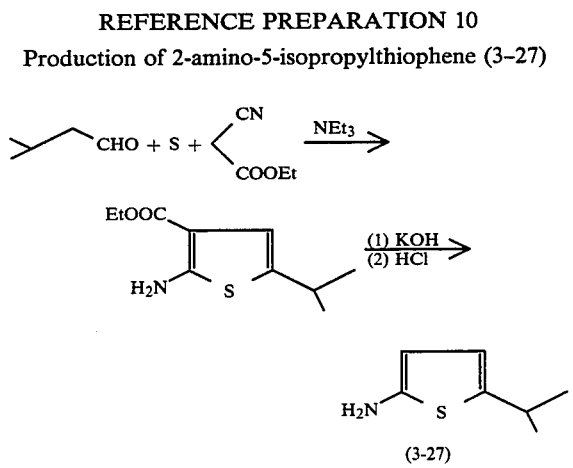

REFERENCE PREPARATION 11

2-Amino-4-propylthiophene

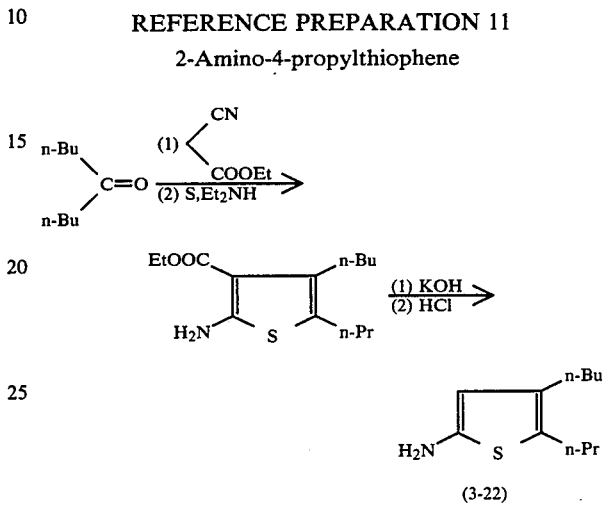

wherein Et and Bu each is the same as above and Pr represents propyl

To a suspension of 17.0 g (0.15 mol) of ethyl cyanoacetate and 4.8 g (0.15 mol) of sulfur in 17 ml dimethylformamide (DMF) is dropwise added 12 ml of triethylamine while being stirred at room temperature. 12.9 g (0.15 mol) of isovaleroaldehyde is dropwise added to the mixture at 30°–40° C. The reaction mixture is stirred at room temperature for 2 hours, combined with ice water, and extracted with ethyl ether. The ether layer is washed with water, dried over magnesium sulfate, and evaporated to leave a residue, which is chromatographed on a silica gel column to give 26.0 g (yield 81.4%) of an oily product. A mixture of the oily product with a solution of 14 g (0.244 mol) of potassium hydroxide in 140 ml of 50% aqueous methanol is refluxed under heating for 2 hours and then evaporated. The remaining aqueous portion is treated with active carbon and acidified with acetic acid under cooling to precipitate crystals, which are then collected by filtration. To a solution of the crystals in 180 ml of methanol is dropwise added 4.5 ml of con. hydrochloric acid while being stirred at 60° C., and the mixture is refluxed under heating for 10 minutes. After cooling, water is added thereto and the methanol is removed by evaporation in vacuo. The residue is washed with ethyl ether, neutralized with 15 ml of 20% aqueous solution of sodium hydroxide while being cooled under nitrogen atmosphere, and then extracted with ethyl ether. The ether layer is washed with water, dried over magnesium sulfate, and the ethyl ether is evaporated. The residue is distilled in vacuo to give 6.3 g (yield 36.6%) of the titled compound (3)' as a pale yellow oil, bp. 83° C. (0.9 mmHg).

IR(film) νmax: 3310, 3190 cm⁻¹.

NMR(CDCl₃) δppm: 1.25 (d, 6H), 2.99 (m, 1H), 3.43 (NH₂), 6.00 (d, 1H), 6.34 (m, 1H).

A mixture of 14.1 g (0.099 mol) of di-n-butyl ketone, 11.2 g (0.099 mol) of ethyl cyanoacetate, 1.54 g of ammonium acetate, and 4.8 g of acetic acid with 30 ml of benzene is refluxed under heating for 64 hours, then cooled. The reaction mixture is washed with a dil. aqueous solution of sodium hydroxide under cooling, dried over magnesium sulfate, and evaporated. The resulting residue is distilled in vacuo to give 20.3 g of an yellow oil, bp. 130° C. (1.5 mmHg). To a suspension of the oily product and 2.74 g (0.085 mol) of sulfur in 20 ml of ethanol is dropwise added 5 ml of diethylamine at room temperature, and the mixture is stirred at 60° C. for 17 hours and evaporated to leave a residue, which is chromatographed on a silica gel column (with methylene chloride) to give 22.5 g (yield 84.5%) of the intermediate as an yellow oil.

NMR(CDCl₃) δppm: 0.77–1.82 (m, 15H), 2.61 (m, 4H), 4.29 (q, 2H), 5.97 (NH₂).

To 0.683 g (2.54 mmol) of the intermediate is added a solution of 0.33 g of potassium hydroxide in 80% methanol (2.5 ml), and the mixture is refluxed under heating for 5 hours. The reaction mixture is evaporated to leave a residue, which is dissolved in ice water. The solution is washed with ethyl ether and neutralized with acetic acid to precipitate crystals, which are collected by filtration. To a solution of the crystals in 5 ml of n-propanol is dropwise added 0.5 ml of conc. hydrochloric acid at 65° C. and then the mixture stirred at 60° C. for 3 minutes. The solvent is removed and the resulting residue is combined with ice water, washed with ethyl ether, alkalized with 20% aqueous solution of sodium hydroxide, and extracted with ethyl ether. The ethyl ether layer is washed with water, dried over magnesium sulfate, and evaporated to give 0.289 g (yield 57.4%) of the crude titled compound (3-22) as yellow oil.

IR(film) νmax: 3175, 3300 cm⁻¹.

NMR(CDCl₃) δppm: 0.70–2.72 (m, 16H), 3.50 (NH₂), 5.90 (s, 1H).

REFERENCE PREPARATION 12

Production of
2-amino-4-cyclopentylmethyl-5-methylthiophene
(3–20)

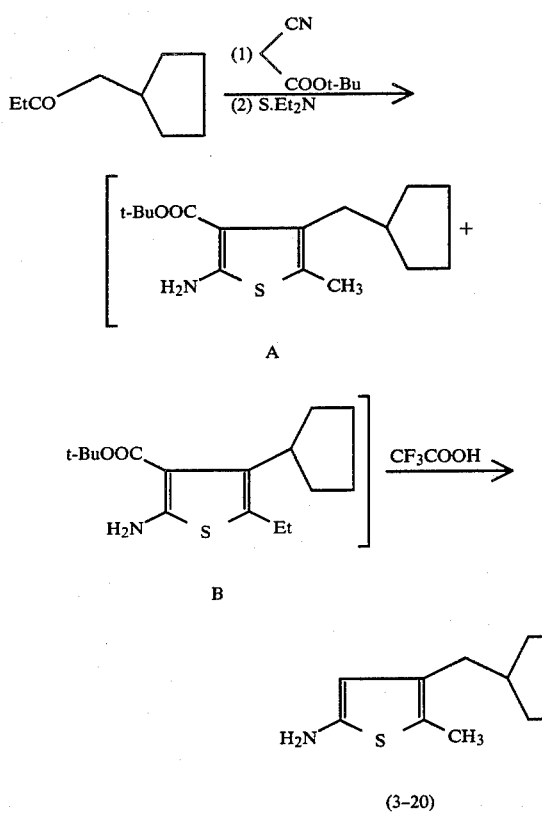

A mixture of 1.93 g (0.0137 mol) of 1-cyclopentyl-2-butanone, 1.94 g (0.0137 mol) of t-butyl cyanoacetate, 5 ml of benzene, 0.2 g of ammonium acetate, and 0.6 g of acetic acid is refluxed under heating for 20 hours while being dehydrated. After cooled, the reaction mixture is washed with dil. aqueous solution of sodium hydrogencarbonate, dried over magnesium sulfate, and evaporated. The resulting residue is distilled in vacuo to give 17 g of a colorless oil, bp. 50° C. (0.1 mmHg).

To a mixture of the oil with 2 ml of t-butanol and 0.26 g of sulfur is dropwise added 0.5 ml of diethylamine while being stirred at room temperature. The reaction mixture is stirred at 60° C. for 18 hours and evaporated to give a residue, which is chromatographed on a silica gel column (with benzene) to give 2.21 g (yield 55.2%) of the intermediates A and B (as a mixture) as an yellow oil.

A solution of 1.11 g (3.76 mmol) of the intermediates (a mixture of A and B) in 5 ml of trifluoroacetic acid is stirred at room temperature for 30 minutes, then 60° C. for 1.5 hours, and the solvent is removed. The residue is dissolved in ethyl ether, washed with a dil. aqueous solution of sodium hydrogencarbonate, and extracted with 1N-hydrochloride acid. The aqueous layer is neutralized with an aqueous solution of sodium hydrogencarbonate and then extracted with ethyl ether. The organic layer is evaporated to give a residue, which is chromatographed on a silica gel column (with methylene chloride) to give 415 mg (yield 56.5%) of the titled compound (3–20) as an yellow oil.

NMR(CDCl₃), δppm: 1.00–2.58 (m, 9H), 2.17 (s, 3H), 2.34 (d, 2H), 3.72 (NH₂), 5.92 (s, 1H).

REFERENCE PREPARATION 13

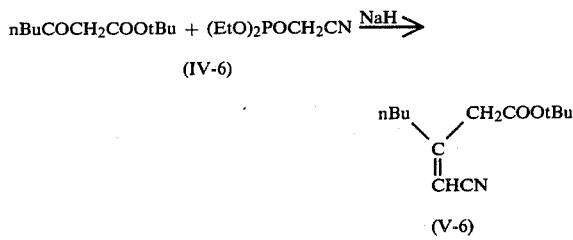

To a suspension of 0.4 g (10.6 mmol) of 60% sodium hydride in 6 ml of dimethoxyethane (DME) is dropwise added a solution of 1.77 g (10 mmol) of diethyl cyanomethylphosphonate in DME (4 ml) while being stirred under ice-cooling. After the addition, the reaction mixture is further stirred at 20° C. for 10 minutes. A solution of 2.0 g (10 mmol) of the starting material (IV-6) in 2 ml of DME is added thereto and the mixture is refluxed under heating for 4 hours, then cooled. The reaction mixture is combined with ice water and extracted with ethyl ether. The ether layer is washed with a dil. aqueous solution of sodium hydroxide, then water, dried over magnesium sulfate, and filtered. The mother liquor is evaporated in vacuo to give 1.972 g (yield 88.3%) of the objective compound (V-6) as a colorless oil, bp. 80°–90° C. (0.1 mmHg). This is a mixture of Z- and E-forms of the objective compound.

NMR(CDCl₃) δppm: 0.8–1.6 (m, 7H), 1.44 (s, 9H), 2.28 (t) 2.49 (t) (2H), 3.08 (d) 3.34 (s) (2H), 5.27 (d, 1H).

REFERENCE PREPARATION 14

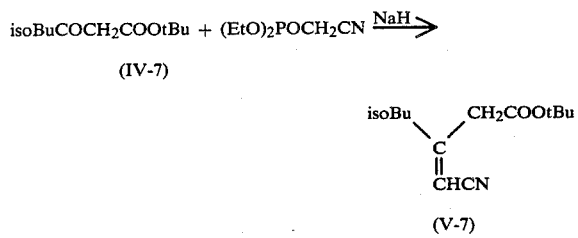

In the same manner as shown above, the reaction is performed by using a suspension of 8.06 g (0.168 mol) of 50% sodium hydride in 160 ml of DME, a solution of 28.0 g (0.158 mol), of diethyl cyanomethylphosphonate in 127 ml of DME, and a solution of 31.7 g (0.158 mol) of the starting material (IV-7) in 63 ml of DME to give 23.4 g (yield 66.2%) of the objective compound (V-7) as a colorless oil, bp. 85° C. (0.25 mmHg). This is a mixture of Z- and E-forms of the objective compound.

NMR(CDCl₃) δppm: 0.89 (d) 0.96 (d) (6H), 1.46 (s, 9H), 1.95 (m, 1H), 2.15 (d) 2.37 (d) (2H), 3.07 (s) 3.33 (s) (2H), 5.26 (s) 5.35 (s) (1H).

What is claim is:

1. A 4,7-dihydrothieno[2,3-b]pyridine derivative of the formula:

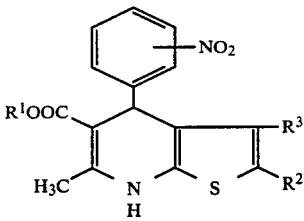

wherein $R^1$ is straight or branched chain $C_1$-$C_4$ alkyl, alkoxyalkyl, or phenyl($C_1$-$C_5$)alkyl; $R^2$ is hydrogen, straight or branched chain $C_1$-$C_4$ alkyl, or alkoxycarbonyl; $R^3$ is hydrogen, straight or branched chain $C_1$-$C_4$ alkyl, phenyl which may be substituted by one or more halogens or alkoxy groups, cycloalkyl, or cycloalkylalkyl; or $R^2$ and $R^3$ taken together may form a $C_3$-$C_6$ alkylene.

2. The compound claimed in claim 1, methyl 4,7-dihydro-6-methyl-4-(3-nitrophenyl)-3-phenyl-thieno[2,3-b]pyridine-5-carboxylate.

3. The compound claimed in claim 1, methyl 4,7-dihydro-6-methyl-4-(3-nitrophenyl)-3-n-butyl-thieno[2,3-b]pyridine-5-carboxylate.

4. The compound claimed in claim 1, methoxyethyl 4,7-dihydro-6-methyl-4-(3-nitrophenyl)-3-n-butyl-thieno[2,3-b]pyridine-5-carboxylate.

5. The compound claimed in claim 1, methyl 4,7-dihydro-6-methyl-4-(3-nitrophenyl)-3-isobutyl-thieno[2,3-b]pyridine-5-carboxylate.

6. The compound claimed in claim 1, methoxyethyl 4,7-dihydro-6-methyl-4-(3-nitrophenyl)-3-isobutyl-thieno[2,3-b]pyridine-5-carboxylate.

7. The compound claimed in claim 1, methyl 4,7-dihydro-6-methyl-4-(3-nitrophenyl)-3-cyclopentylmethylthieno[2,3-b]pyridine-5-carboxylate.

8. The compound claimed in claim 1, methyl 4,7-dihydro-6-methyl-4-(3-nitrophenyl)-3-cyclohexyl-thieno[2,3-b]pyridine-5-carboxylate.

9. A composition for treatment of cardiovascular diseases containing inert diluents and a therapeutically effective amount of a compound of the formula:

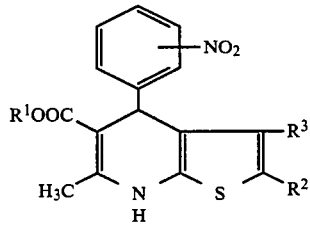

wherein $R^1$ is straight or branched chain $C_1$-$C_4$ alkyl, alkoxyalkyl, or phenyl($C_1$-$C_5$)alkyl; $R^2$ is hydrogen, straight or branched chain $C_1$-$C_4$ alkyl, or alkoxycarbonyl; $R^3$ is hydrogen, straight or branched chain $C_1$-$C_4$ alkyl, phenyl which may be substituted by one or more halogens or alkoxy groups, cycloalkyl, or cycloalkylalkyl; or $R^2$ and $R^3$ take together may form a $C_3$-$C_6$ alkylene.

* * * * *